(12) United States Patent
Xu

(10) Patent No.: US 6,859,276 B2
(45) Date of Patent: Feb. 22, 2005

(54) EXTRACTED POLARIZATION INTENSITY DIFFERENTIAL SCATTERING FOR PARTICLE CHARACTERIZATION

(75) Inventor: Renliang Xu, Pembroke Pines, FL (US)

(73) Assignee: Coulter International Corp., Miami, FL (US)

( * ) Notice: Subject to any disclaimer, the term of this patent is extended or adjusted under 35 U.S.C. 154(b) by 225 days.

(21) Appl. No.: 10/350,770

(22) Filed: Jan. 24, 2003

(65) Prior Publication Data

US 2004/0144935 A1 Jul. 29, 2004

(51) Int. Cl.[7] .............................................. G01N 15/02
(52) U.S. Cl. .................... 356/336; 356/339; 356/340; 356/342; 356/343; 356/365
(58) Field of Search ................................ 356/335, 336, 356/337, 338, 339, 340, 341, 342, 343, 364, 365

(56) References Cited

U.S. PATENT DOCUMENTS

| | | | |
|---|---|---|---|
| 4,953,978 A | 9/1990 | Bott et al. | |
| 5,056,918 A | 10/1991 | Bott et al. | |
| 5,104,221 A | 4/1992 | Bott et al. | |
| 5,229,839 A | * 7/1993 | Hayashi et al. | ............. 356/336 |
| 6,252,658 B1 | * 6/2001 | Togawa et al. | ............. 356/335 |

* cited by examiner

Primary Examiner—Gregory J. Toatley Jr.
Assistant Examiner—Roy M. Punnoose
(74) Attorney, Agent, or Firm—Warren W. Kurz; Mitchell E. Alter

(57) ABSTRACT

A particle sizing method and apparatus of the PIDS type uses randomly polarized radiation to irradiate a particle sample. Portions of the resulting side scattering pattern are decomposed to simultaneously produce, for each decomposed portion, first and second linearly polarized beams of radiation in which the respective planes of polarization of the two beams are mutually perpendicular. Each of the polarized beams is focused onto a photodetector, and the respective photodetector outputs are differentiated to provide PIDS signals that are useful in calculating a particle size distribution for the sample.

12 Claims, 2 Drawing Sheets

EXTRACTED POLARIZATION INTENSITY DIFFERENTIAL SCATTERING FOR PARTICLE CHARACTERIZATION

BACKGROUND OF THE INVENTION

1. Field of the Invention

The present invention relates to methods and apparatus for measuring the size and size distribution of small particles in suspension. More particularly, it relates to improvements in such methods and apparatus in which the particle size and distribution is at least partially determined by measuring the respective intensities of scattered polarized radiation in two mutually perpendicular planes.

2. Discussion of the Prior Art

Being able to characterize small particles in a suspension or spray in terms of size and size distribution is often useful in carrying out research, development and quality control in many industries. Laser diffraction, based on Mie scattering theory or Fraunhofer diffraction theory, is commonly used to size small particles (typically micron-sized particles and larger) on the basis of the light-scattering intensity patterns produced by the particles irradiated by a monochromatic beam of radiation. Laser diffraction is a particularly popular particle-sizing technique due to its relatively broad particle-sizing range, its reproducibility, and the speed of analysis it facilitates. The foundation of such analysis is based on the fact that each particle irradiated by a monochromatic beam produces a characteristic scattering pattern that is determined, in part, by the particle size. Generally, larger particles scatter more light than do smaller particles, and the intensity of the scattering pattern decreases with increasing scattering angle according to a characteristic periodic pattern of minima and maxima. As the particle size gets smaller, the overall intensity of the scattering pattern decreases, as does the contrast between the minima and maxima. For particles in the sub-micron size range, the angular scattering intensity contrast is very small, making particle size retrieval difficult. As the particle size approaches the wavelength of the irradiating energy, the scattering patterns are virtually indistinguishable, and particle sizing can no longer be effected by laser diffraction.

Due to the above-noted particle size limitation that is inherent in the laser diffraction technique for sizing particles, other methods have been used for sizing particles in the sub-micron range. One such method is known as the Polarization Intensity Differential Scattering or "PIDS" method. It makes use of the fact that sub-micron particles will scatter an incident, linearly polarized beam of radiation in such a manner as to produce a characteristic scattering pattern that is dependent not only on the wavelength of the irradiating beam, but also on the direction of polarization of the beam. Thus, the scattering pattern produced by a horizontally polarized beam (i.e., a beam polarized in a direction parallel to a scattering plane defined by the incident beam and the scattered beam(s)) will differ markedly from that produced by a vertically polarized beam (i.e., a beam polarized in a direction perpendicular to such scattering plane). By determining the difference in intensities of the two scattering patterns (i.e., one pattern produced by a parallel polarized beam and the other produced by a perpendicularly polarized beam) over a relatively wide angular range and at different wavelengths of the incident beams, the PIDS technique has been successfully applied in sizing submicron particles of various materials as small as about 40 nanometers.

According to the known PIDS technology, as described, for example, in the commonly assigned U.S. Pat. No. 4,953,978 to Bott et al., a vertically polarized beam (i.e., polarized perpendicular to the intended scattering plane) of radiation of a chosen wavelength irradiates particles of interest. The intensity of radiation scattered by the particles is measured at several scattering angles, preferably centered about 90 degrees with respect to the direction of propagation of the irradiating beam. The direction of polarization of the irradiating beam is then changed by ninety degrees so as to be horizontally polarized, (i.e., parallel to the scattering plane), and the scattering measurements are made again. This process is then repeated using beams of radiation at different wavelengths. The results of these sequential measurements are processed according to a known algorithm to provide a particle size distribution for the particles of interest. It may be appreciated that the accuracy of this process ideally requires that the sequential measurements be made from the same particles. Since the particles will have a tendency to move between successive measurements, the suspension is continually circulated during the measurement process to assure its homogeneity. Further, each of the several measurements is accumulated over a period of time. Thus, the PIDS process, while being capable of sizing particles too small to be detected by the more conventional laser diffraction method, tends to be relatively time consuming.

SUMMARY OF THE INVENTION

In view of the foregoing discussion, an object of this invention is to substantially reduce the time required to size small particles by the afore-described PIDS technique.

The present invention makes use of the phenomenon that optically isotropic, non-optically-active particles of the type that are commonly found or used in many particle suspensions of interest act to scatter radiation without altering its polarization characteristics. Thus, for example, vertically polarized radiation incident on such particles will be scattered as vertically polarized radiation; similarly, incident randomly polarized radiation will remain randomly polarized after scattering. In accordance with a first aspect of the invention, a method for determining the size distribution of particles of different sizes contained in a liquid suspension of such particles comprises the steps of: (a) irradiating a liquid suspension of particles with a beam of randomly polarized, monochromatic radiation of a predetermined wavelength to produce randomly polarized scattered radiation at a plurality of scattering angles; (b) simultaneously decomposing the randomly polarized scattered radiation into two linearly polarized beams of mutually perpendicular polarization relative to a scattering plane; (c) simultaneously sensing the respective intensities of each of the linearly polarized beams to produce a PIDS signal representing the difference in such intensities; and (d) determining the size distribution of particles in the suspension on the basis of the PIDS signal. Preferably, the decomposing step is effected by passing the scattered radiation through a birefringent material. Since the two signals representing the respective intensities of the linearly polarized beams are produced simultaneously rather than in sequence, as is the case of the prior art, the processing time for providing the data necessary for a particle size distribution is effectively halved; further, the two signals are produced by scattering from the exact same particles in the suspension or sample. To enhance the reliability of the process and the sizing resolution, steps (a) through (c) are repeated using at least one, and more preferably two or more, irradiating beams of differing wavelength.

According to a second aspect of the invention, a new and improved PIDS-type apparatus is provided for characterizing particles in suspension. Such apparatus comprises: (a) illumination means for sequentially irradiating the liquid suspension of particles with at least two beams of randomly polarized, monochromatic radiation of different wavelengths to produce two scattering patterns of randomly polarized scattered radiation of different wavelengths; (b) decomposing means for decomposing selected portions of each of the scattering patterns to produce a plurality of linearly polarized beams of mutually perpendicular polarization relative to a scattering plane; (c) sensing means for simultaneously sensing the intensity of each of the linearly polarized beams; and (d) determining means for determining the size distribution of particles in the suspension on the basis of the difference of the sensed intensities of the linearly polarized beams.

The invention and its advantages will become more evident from the ensuing detailed description of preferred embodiments, reference being made to the accompanying drawings in which like reference characters denote like parts.

DETAILED DESCRIPTION OF PREFERRED EMBODIMENTS

Figure 1:
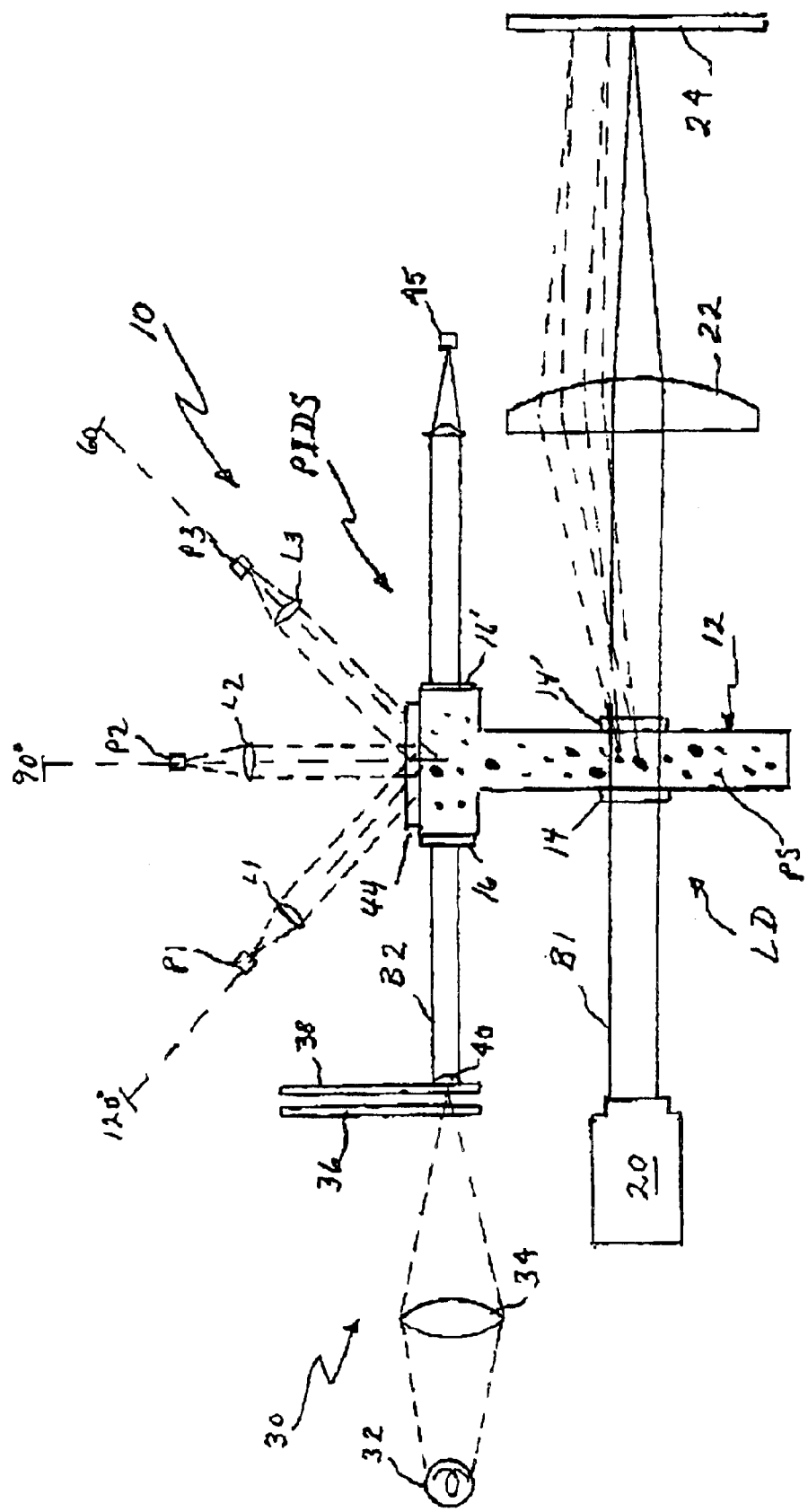
FIG. 1 is a schematic illustration of a small particle characterization apparatus structured in accordance with the prior art.

Referring now to the drawings, FIG. 1 schematically illustrates components of a conventional particle sizing instrument 10 that embodies both laser diffraction and PIDS technology. The instrument shown is of the type manufactured by Beckman Coulter, Inc., and sold as its LS™ Series instrument. Such an instrument typically comprises a sample chamber 12 that is adapted to receive a liquid particle suspension PS comprising particles of interest. The sample chamber has two pair of windows 14, 14' and 16,16' through which the contained sample can be irradiated by different beams of radiation for the purpose of producing a different scattering patterns, discussed below. The laser diffraction component LD of instrument 10 comprises a continuous wave laser 20 that serves to irradiate the particle suspension through the front window 14 of the sample chamber with a beam B1 of monochromatic and spatially coherent radiation. Forwardly scattered light from the irradiated sample passes through the rear window 14' and is collected by a Fourier lens system 22. The latter serves to focus radiation scattered through a relatively small angular range (e.g. plus or minus 10 degrees) onto a photodetector array 24. The latter serves to detect the forward scattering pattern at selected angles within the forward scattering range, and its output is processed, in a conventional manner, to provide a size distribution of particles in the sample. Details of the laser diffraction technique for sizing particles are disclosed in the above-noted U.S. Pat. No. 4,953,978, the contents of which are incorporated herein by reference.

As indicated above, the effectiveness of the laser diffraction component of the FIG. 1 instrument is limited to some extent by particle size, such component being limited to detecting particles having a size greater than about 0.5 microns. To size particles in the size range of between about 0.05 microns and 1 micron, instrument 10 further includes a PIDS component. The latter comprises a beam-producing portion 30 for selectively producing a substantially monochromatic and linearly polarized beam B2. Portion 30 comprises a white light source 32, typically a tungsten lamp, for producing polychromatic and non-polarized radiation, and a condensing lens 34 for directing a portion of such radiation through the respective optical filter elements of a polarizing filter wheel 36 and a color filter wheel 38. The polarizing filter wheel 36 comprises two polarizing filter elements, not shown. One such element is adapted to linearly polarize, say, a horizontal direction, i.e., parallel to the scattering plane, any randomly polarized radiation passing through it. Similarly, the other polarizing filter element is adapted to linearly polarize incident radiation in a vertical direction, perpendicular to the scattering plane and, hence, perpendicular to the direction of polarization of the radiation incident on the first filter element. The color filter wheel 38 typically contains, for example, three different optical bandpass filters, each being adapted to pass substantially monochromatic radiation centered at one of three different wavelengths, e.g., 450 nanometers, 600 nanometers and 900 nanometers. Radiation passing through both filter wheels is collimated by a lens 40 to produce a beam B2 which, at any given time, may be, for the example given, any one of three different colors, and either of two linear polarities, depending on the filtering elements through which the beam radiation has passed. Upon entering the sample chamber and irradiating the particles therein, beam B2 produces a pattern of side-scattered radiation, centered at a scattering angle of 90 degrees. Such radiation emerges from the sample chamber through an optical window 44 located in a side wall of the sample chamber. Assuming the particles are irradiated by six different beams B2, i.e., three different colors, each being either horizontally or vertically polarized, six different side scattering patterns will be created. A plurality of lenses L1–L3 are positioned to collect radiation from different portions of the side scattering patterns and to focus the collected radiation onto a like plurality of photodetectors P1–P3 (only three being shown for the sake of illustration). The lens/photodetector combinations operate to detect the intensity of the side scattering patterns at scattering angles of 90 degrees, and at strategic equal angles (e.g., plus and minus 30 degrees) on opposite sides of the 90 degree detector. Further, a beam intensity monitor 45 is positioned on the optical axis of beam B2 to monitor fluctuations in the intensity of the beam passing straight through the sample. The respective outputs of the photodetectors and beam monitor are processed in a known manner to produce the PIDS signals used to provide a particle size distribution for the particles within the sample.

As indicted earlier, the particle-sizing analysis carried out by the instrument of FIG. 1 is relatively time-consuming in that multiple measurements are made sequentially, one for each beam color/polarization combination. While multiple measurements operate to increase the resolution of the particle size distribution provided, it also increases the uncertainty of the results since each measurement is made on a sample that is being circulated through the sample chamber to maintain its homogeneity during the measurements. Thus, ideally, the number of measurements should be minimized without sacrificing the resolution of the particle distribution.

Figure 2:
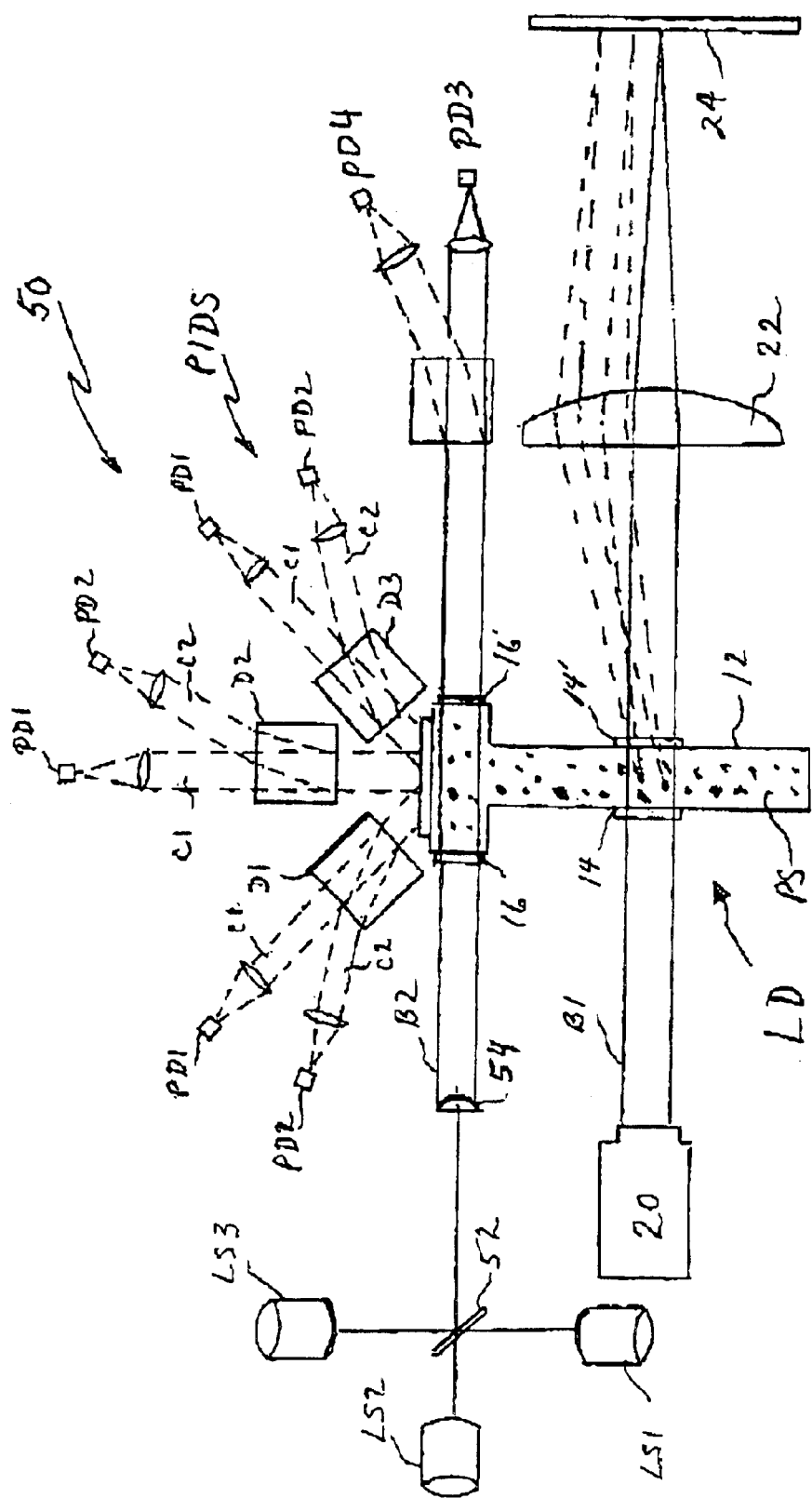
FIG. 2 is a schematic illustration of a small particle characterization apparatus embodying the present invention.

Now in accordance with the present invention, the number of sequential measurements made in a PIDS-type particle-sizing instrument of the FIG. 1 type is reduced by fifty percent while maintaining the resolution at a desired value. Referring to FIG. 2, a particle-sizing instrument 50 embodying the present invention is also shown as comprising a laser diffraction LD component and a PIDS component. The LD component is the same as described above and needs no further comment. The PIDS component, however, differs from the FIG. 1 instrument in that the two linearly polarized beam elements (horizontally and vertically polarized) required to produce PIDS signals are produced after beam B2 has interacted with the particle sample. More importantly, the two linearly polarized components are produced simultaneously, rather than sequentially, as in the case of the prior art.

Referring again to FIG. 2, the light source from which the particle-irradiating beam B2 is produced may, as in the FIG. 1 instrument, comprise a white light source that is suitably filtered through a color filter wheel or the like to sequentially provide multiple monochromatic beams of different color and random polarization. More preferably, however, beam B2 is produced by any one of three different light sources LS1–LS3, each preferably being either a light-emitting diode or a laser adapted to provide randomly polarized light (radiation). By "randomly polarized", it is meant that the emitted radiation comprises both horizontal and vertical components of polarization. Each of the light sources is designed to emit at one of three different wavelengths $\lambda 1$, $\lambda 2$ and $\lambda 3$. The position of mirror 52 determines which of the three different light sources is directed to a beam-expanding lens system 54 that also serves to collimate the irradiating beam B2. Importantly, each of the light sources LS provides a randomly polarized output beam. Assuming the particles in the sample are optically isotropic and not optically active, they will produce, upon being irradiating by the randomly polarized beam B2, a scattering pattern of randomly polarized radiation.

According to the invention, predetermined portions of the above-noted side scattering pattern of randomly polarized radiation are decomposed by a plurality of decomposing elements D1–D3 positioned at strategic locations in the scattering pattern. Each of these decomposing elements operates to decompose the randomly polarized radiation incident thereon into its constituent, mutually perpendicular, linearly polarized components, C1 and C2. Each of the two linearly polarized components from each of the decomposing elements is brought to focus onto one of a pair of photodetectors PD1 and PD2, and the respective outputs of these detectors are subtracted to provide a PIDS signal for analysis. Similarly, the randomly polarized beam passing through the sample is decomposed into its constituent horizontal and vertical polarization components, which are detected by a photodetector pair, PD3 and PD4. The PIDS signals and the outputs from the beam monitor are processed in a known manner to provide the particle distribution of interest.

The decomposing elements D1–D3 may take any one of several forms. Preferably, however, each of these elements comprises a birefringent material in the form of either a conventional Wollaston prism, a Glan prism or a Thompson prism.

From the foregoing, it will be appreciated that the method and apparatus of the invention significantly reduces the processing time required to produce the PIDS signals used for providing a particle size distribution for the sample of interest. Since both of the polarization measurements required for producing each of the PIDS signals are made simultaneously, rather than in sequence, the processing time can be reduced by at least 50 percent compared to the processing time of the prior art method discussed above. More importantly, for each wavelength of the irradiating source, the two different polarization measurements needed to provide each of the PIDS signal are obtained from the exact same particles in the sample. This has the effect, of course, of significantly increasing the reliability of the resulting particle size distribution.

While the invention has been described with reference to certain preferred embodiments, it will be appreciated that various modifications will become self-evident to those skilled in the art, and such modifications are intended to fall within the scope of the appended claims.

What is claimed is:

1. A method for determining the size distribution of particles of different sizes contained in a mass of such particles, said method comprising the steps of:
    (a) irradiating said mass of particles with a beam of randomly polarized, monochromatic radiation of a predetermined wavelength to produce a side scattering pattern of randomly polarized radiation;
    (b) simultaneously decomposing each of a plurality of selected portions of said side scattering pattern into first and second linearly polarized beams of mutually perpendicular polarization direction;
    (c) determining the difference in intensity of said first and second linearly polarized beams to produce a PIDS signal for each of said plurality of selected portions of said side scattering pattern; and
    (d) using said PIDS signals to determine the size distribution of particles in said mass.

2. The method as defined by claim 1 wherein steps (a) through (c) are repeated for each of one or more additional beams of different wavelength to provide additional PIDS signals that enhance the resolution of the particle size distribution.

3. The method as defined by claim 1 wherein said decomposing step is effected by passing said each of said selected portions through a birefringent material.

4. The method as defined by claim 3 wherein said birefringent material comprises a Wollaston prism.

5. The method as defined by claim 3 wherein said birefringent material comprises a Glan prism.

6. The method as defined by claim 3 wherein said birefringent material comprises a Thompson prism.

7. The method as defined by claim 1 further comprising the steps of (e) decomposing the randomly polarized irradiating beam after said beam irradiates said particle mass to produce a pair of linearly polarized beams of mutually perpendicular polarization directions; (f) sensing the respective intensities of said pair of linearly polarized beams; and (g) using the respective sensed intensities with said PIDS signals to determine said particle size distribution.

8. Apparatus for characterizing particles in a mass of such particles, said apparatus comprising:
    (a) illumination means for sequentially irradiating the mass of particles with a beam of randomly polarized, monochromatic radiation of predetermined wavelength to produce a side scattering pattern of randomly polarized radiation;
    (b) decomposing means for decomposing selected portions of said randomly polarized scattering pattern to produce a pair of linearly polarized beams of mutually perpendicular polarization directions for each of said selected portions;
    (c) photosensing means for simultaneously sensing the intensity of each of the linearly polarized beams; and
    (d) determining means for determining the size distribution of particles in the mass on the basis of the difference of the sensed intensities of the linearly polarized beams.

9. The apparatus as defined by claim 8 wherein said decomposing means comprises a birefringent material positioned in said each of said selected portions of said scattering patterns.

10. The apparatus as defined by claim 8 wherein said birefringent material comprises a Wollaston prism.

11. The apparatus as defined by claim 8 wherein said birefringent material comprises a Glan prism.

12. The apparatus as defined by claim 8 wherein said birefringent material comprises a Thompson prism.

* * * * *